United States Patent [19]

Benkö et al.

[11] 4,373,101
[45] Feb. 8, 1983

[54] QUINOXALINE-2-YL ETHENYL KETONES

[75] Inventors: Pal Benkö; Daniel Bozsing; János Gundel; Károly Magyar, all of Budapest, Hungary

[73] Assignee: Egyt Gyogyszervegyeszeti Gyar, Budapest, Hungary

[21] Appl. No.: 269,721

[22] Filed: Jun. 2, 1981

[30] Foreign Application Priority Data

Jun. 3, 1980 [HU] Hungary .............................. 1385/80

[51] Int. Cl.³ ............................................ C09B 55/00
[52] U.S. Cl. .................................. 542/440; 424/250; 426/532
[58] Field of Search ....................... 544/353; 424/250; 426/532; 542/440

[56] References Cited

U.S. PATENT DOCUMENTS

| | | | |
|---|---|---|---|
| 3,818,007 | 6/1974 | Cronin et al. | 544/353 |
| 3,900,473 | 8/1975 | Diel et al. | 544/353 |
| 4,038,392 | 7/1977 | Urban | 544/353 |
| 4,303,657 | 12/1981 | Young et al. | 544/353 |

OTHER PUBLICATIONS

Matoba K. et al., Chem. & Pharm. Bulletin, vol. 29 #6, Sep. 1981, pp. 2442-2450.

*Primary Examiner*—Paul J. Killos
*Attorney, Agent, or Firm*—Karl F. Ross

[57]     ABSTRACT

The invention relates to novel quinoxaline-2-yl ethenyl ketones, their preparation and compositions containing them.

The novel quinoxaline-2-yl ethenyl ketones of the general formula I

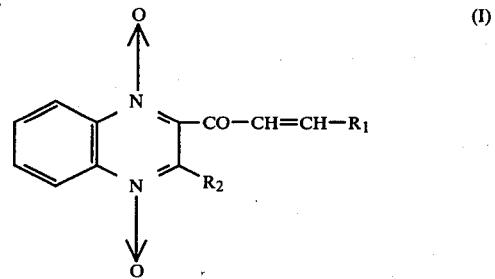

wherein
$R_1$ represents an aryl group or a heterocyclic group comprising one or more nitrogen and/or oxygen and/or sulfur atoms wherein both the aryl and heterocyclic groups are optionally substituted by one or more identical or different substituents,
$R_2$ stands for a hydrogen atom or a $C_{1-4}$ alkyl group, are prepared by reacting an acetylquinoxaline derivative of the general formula II

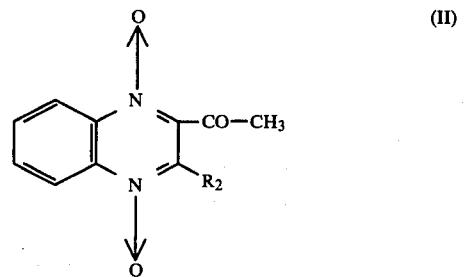

wherein $R_2$ is as stated above, with an aldehyde of the general formula III $R_1$—CHO         (III)

wherein $R_1$ is as stated above.

The novel compounds of the general formula I possess valuable antibacterial effect and promote the growth of animals. Thus, the novel compounds can be incorporated in animal feeds.

8 Claims, No Drawings

QUINOXALINE-2-YL ETHENYL KETONES

The invention relates to novel quinoxaline-2-yl ethenyl ketones, their preparation and compositions containing them.

More particularly, the invention relates to quinoxaline-2-yl ethenyl ketones of the formula I

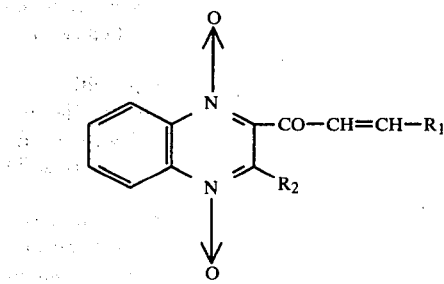

wherein $R_1$ represents an aryl group or a heterocyclic group comprising one or more nitrogen and/or oxygen and/or sulfur atoms, wherein both the aryl and heterocyclic groups may be substituted by one or more identical or different substituents, and $R_2$ is hydrogen atom or $C_{1-4}$ alkyl.

The novel compounds possess valuable antibacterial effects and promote the growth of animals. Thus, the novel compounds can be incorporated in animal feeds.

In the formula I the aryl group is preferably a phenyl, alpha-naphthyl or beta-naphthyl. The aryl group is optionally substituted by one or more identical or different substituents such as halogen, for example fluorine, chlorine, bromine or iodine; hydroxy; $C_{1-4}$ alkyl, for example methyl, ethyl, n-propyl, isopropyl, n-butyl, sec.-butyl, tert.-butyl or isobutyl; or $C_{1-4}$ alkoxy, for example methoxy, ethoxy, n-propoxy, isopropoxy, n-butoxy, sec.-butoxy, tert.-butoxy or isobutoxy.

The heterocyclic group may comprise one or more nitrogen and/or oxygen and/or sulfur atoms as heteroatoms. The nucleus comprising the heteroatoms may be condensed with one or more benzene and/or further heterocyclic rings. Optionally, both the heterocyclic and benzene nuclei may be substituted by one or more identical or different substituents such as halogen, for example fluorine, chlorine, bromine or iodine; hydroxy; $C_{1-4}$ alkyl, for example methyl, ethyl, n-propyl, n-isopropyl, n-butyl, sec.-butyl, tert.-butyl or isobutyl; or $C_{1-4}$ alkoxy, for example methoxy, ethoxy, propoxy, isopropoxy, n-butoxy, sec.-butoxy, tert.-butoxy or isobutoxy.

A subclass of the compounds of the invention consists of the quinoxaline-2-yl ethenyl ketones of the formula I wherein $R_1$ is phenyl or phenyl substituted with one to three substituents selected from the group consisting of halogen, $C_{1-4}$ alkoxy or hydroxy, or a naphthyl group or a heterocyclic group comprising one to two ring nitrogen and/or oxygen atoms and having one or two nuclei optionally substituted by one or two $C_{1-4}$ alkyl groups, $R_2$ stands for a hydrogen atom or a $C_{1-4}$ alkyl group.

Preferred compounds of the invention are as follows: 3-Methylquinoxaline-2-yl-1,4-dioxide phenylethenyl ketone and 3-Methylquinoxaline-2-yl-1,4-dioxide quinoxaline-2-yl-ethenyl ketone.

The quinoxaline-2-yl ethenyl ketones of the formula I are prepared by reacting an acetylquinoxaline derivative of the formula II

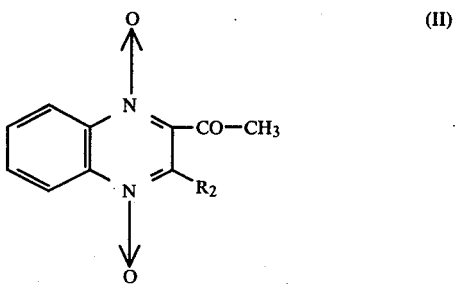

wherein $R_2$ is as stated above, with an aldehyde of the formula III $$R_1\text{-CHO} \qquad (III)$$

wherein $R_1$ is as stated above.

The reaction of the acetylquinoxaline derivative of the formula II with the aldehyde of the formula III can be performed in the presence of a base used as a catalyst. Either an inorganic base such as sodium hydroxide, potassium hydroxide, calcium hydroxide, sodium carbonate, potassium carbonate, or an organic base such as an amine, for example pyridine, piperidine, pyrrolidine, diazabicycloundecene, diazabicyclononene, triethylamine, furthermore an ammonium carboxylate, for example ammonium acetate can be employed.

Preferably, the reaction components are reacted in the presence of piperidine.

If desired, a solvent or diluent may be used, too. The diluent may be an inert organic solvent such as an alkanol, for example methanol, ethanol, isopropanol or butanol; an alkyl ketone, for example acetone or methyl ethyl ketone; an ether, for example diethyl ether, dioxane or tetrahydrofurane; dimethylformamide; an aliphatic or aromatic hydrocarbon, for example hexane, heptane, benzene, toluene, xylene; a chlorinated aliphatic or aromatic hydrocarbon, for example methylene chloride, chloroform, carbon tetrachloride, chlorobenzene, dichlorobenzene; nitrobenzene; acetonitrile; or pyridine. A mixture of two or more solvents can be used as a diluent, too.

If the starting compounds employed do not interact with water, the diluent may also be a mixture of one or more organic solvents and water. An excess of the aldehyde of the formula III can also be employed as a diluent.

The reaction of the acetylquinoxaline derivative of the formula II with the aldehyde of the formula III can be performed within a wide temperature range. In general, the reaction proceeds at a temperature of 0° to 120° C., preferably at 10° to 100° C.

Generally, atmospheric pressure is employed for the reaction, although higher pressures can be used.

One mole of the acetylquinoxaline derivative of the formula II is reacted, in general, with 1 to 3 moles, preferably 1 to 1.1 moles of the aldehyde of the formula III, optionally in the presence of a basic catalyst employed in an amount of 0.01 to 0.2 mole. Of course, other molar ratios can also be used without any adverse effect on the reaction.

In general, the process of the invention is performed as follows:

The acetylquinoxaline derivative of the formula II is dissolved or suspended in a solvent. The aldehyde of the formula III is added, optionally in several portions, and, if desired, a basic catalyst is added, too. However, the acetylquinoxaline derivative can be added to the aldehyde, too.

The quinoxaline-2-yl ethenyl ketones of the formula I separate in crystalline form from the warm reaction mixture or on cooling. However, in some cases it is essential to evaporate the reaction mixture to ensure the separation of the reaction product.

The acetylquinoxaline derivatives of the formula II used as starting compounds can be prepared by known methods [see e.g. J. Org. Chem., 31, 1067]. The aldehydes of the formula III are known compounds.

Due to their valuable antibacterial and growth promotion effect, the novel compounds of the formula I can be used in animal husbandry.

The novel compounds of the formula I exhibit antibacterial activity against both gram-positive and gram-negative bacteria, especially Enterobacteriaceae such as *Escherichia coli,* Pseudomonadaceae such as *Pseudomonas aeruginosa,* Micrococcaceae such as *Staphylococcus aureus* etc. Thus, the novel compounds can be used for treating both local and systemic bacterial infections in animals.

The minimal inhibition concentration of the compounds is between 0.5 and 100 microgram/milliliter.

The weight gain increasing effect of the compounds was tested on pigs as follows. Groups consisting of 6 animals were fed under the same conditions with animal feed of the same amount and composition. In the test groups, the animals received a feed admixed with 50 mg/kg of the compound to be tested, whereas no additive was blended with the feed in the control group. Each test was repeated twice.

The weight gain was determined daily, and the average daily weight gain, in percentage, was calculated by the formula:

$$\frac{\text{daily weight gain in the test group}}{\text{daily weight gain in the control group}} \times 100$$

The quantity of feed consumed during the test was divided by the total weight gain in the test, and the ratio obtained was related to the ratio calculated in the same way for the control group. The result expressed in percentage indicates the quantity of feed producing 1 kg of weight gain in relation to the control group.

The results obtained with the compound prepared in Example 3 are shown in Table I.

TABLE I

| Compound tested | Average daily weight gain, in % | Quantity of feed producing 1 kg of weight gain, in % |
|---|---|---|
| 3-Methylquinoxaline-2-yl-1,4-dioxide phenylethenyl ketone | 122.6 | 80.9 |
| Control | 100 | 100 |

The data of Table 1 clearly demonstrate that the animals fed with the novel compound of the formula I show a significantly higher weight gain than the animals of the control group. Simultaneously, the same weight gain can be obtained by less feed consumption. This fact indicates a considerably favorable feed utilization resulting in economical advantages.

An important advantage of the novel compounds of the formula I is their very high elimination rate, i.e. the novel compounds consumed leave the organism of the animal in a very short time. This results in a considerably shorter withdrawal period (the time lapse following the last administration of the novel compounds until no residue can be detected and the animal is suitable for human consumption).

The quinoxaline-2-yl ethenyl ketones of the formula I have very low toxicity in domestic animals and thus the compounds can be considered to be practically non-toxic.

Furthermore, the invention refers to compositions for use in the animal husbandry comprising an effective amount of the compound of the formula I wherein $R_1$ and $R_2$ are as defined above and one or more inert, solid or liquid carriers.

Compositions suitable for use in the veterinary science such as tablets, coated tablets etc. may be employed. The compositions may contain inert, solid or liquid carriers used in pharmaceutical practice and may be prepared by known methods.

Moreover, the invention refers to animal feeds, feedstuff concentrates and feed additives having antibacterial and/or growth promotion effect which contain a compound of the formula I wherein $R_1$ and $R_2$ are as defined above, and one or more inert, solid or liquid carriers.

The animal feeds of the invention containing an effective amount, in general, 1 to 500 ppm, preferably 10 to 50 ppm of a compound of the formula I are suitable for feeding different domestic animals, especially pig, cattle, sheep and poultry.

The feedstuff concentrates of the invention contain 0.1 to 25 percent of a compound of the formula I in addition to one or more inert, solid or liquid carriers.

Furthermore, the invention refers to a process for the preparation of animal feeds, feedstuff concentrates and feed additives in which a compound of the formula I wherein $R_1$ and $R_2$ are as defined above, is admixed with one or more inert, solid or liquid carriers.

The carrier may be any substance of plant or animal origin which is suitable for animal feeds such as wheat meal, wheat flour, wheat bran, rice bran, soya flour, corn flour, bone meal, meat meal or mixtures thereof. A preferred carrier consists of a fiber-free green plant feed concentrate having high protein content, e.g. VEPEX ®.

Further carriers may be used, too, for example auxiliaries such as wetting agents; antioxidants; starch; mineral substances, for example silica, dicalcium phosphate, calcium carbonate; and sorbic acid.

As wetting agent any non-toxic oil can be employed, preferably soya oil, maize oil or mineral oil. The preferred wetting agents are the alkylene glycols.

The starch employed may be corn starch, wheat starch or potato starch.

Preferably, at first a feedstuff concentrate or pre-mix is prepared comprising 0.1 to 25 percent by weight, especially 10 to 20 percent by weight, of a compound of the formula I and one or more carriers as described above.

A preferred concentrate contains the following components:

Quinoxaline-2-yl ethenyl ketone of the formula I: 0.1–25%
Calcium hydrogen phosphate: 0.01–40%
Calcium carbonate: 0.01–23%

Bone meal and/or lucerne meal: 0.01–12%
Silica: 0.2–1.6%
Antioxidant: 0.1–0.4%
Wetting agent: 1–8%

If desired, the feedstuff concentrate may contain 10 to 25 percent of starch and/or not more than 3 percent of different vitamins.

The feedstuff concentrates may be blended with carriers listed above to give a finished feed containing 1 to 500 ppm, preferably 10 to 50 ppm of a compound of the formula I. The feedstuff concentrates may also be added to animal feeds to produce the finished feed.

Further details of the invention are illustrated by the following non-limiting Examples.

EXAMPLE 1

3-Methylquinoxaline-2-yl-1,4-dioxide phenylethenyl ketone 21.8 g (0.1 moles) of 3-methyl-2-acetylquinoxaline-1,4-dioxide, 10.6 g (0.1 moles) of benzaldehyde and 0.85 g (0.01 moles) of piperidine are reacted in 250 ml of isopropanol at 50° C. for 20 hours. After cooling the product is filtered.

23.9 g (78%) of 3-methylquinoxaline-2-yl-1,4-dioxide phenylethenyl ketone are obtained, m.p.: 187°–188° C.

EXAMPLE 2

3-Methylquinoxaline-2-yl-1,4-dioxide 2,2-dimethyl-6-ethenylbenzo[1,3]dioxanyl ketone 3-Methyl-2-acetylquinoxaline-1,4-dioxide is reacted with 2,2-dimethyl-6-formylbenzo[1,3]dioxane for 3 hours as given in Example 1.

3-Methylquinoxaline-2-yl-1,4-dioxide 2,2-dimethyl-6-ethenylbenzo[1,3]dioxanyl ketone is obtained with a yield of 88%. M.p.: 153°–155° C.

EXAMPLE 3

3-Methylquinoxaline-2-yl-1,4-dioxide quinoxaline-2-yl-ethenyl 1,4-dioxide ketone 3-Methyl-2-acetylquinoxaline-1,4-dioxide is reacted with 2-formylquinoxaline-1,4-dioxide for 8 hours as described in Example 1.

3-Methylquinoxaline-2-yl-1,4-dioxide quinoxaline-2-yl-ethenyl 1,4-dioxide ketone is obtained with a yield of 98%. M.p.: 340° C.

EXAMPLE 4

3-Methylquinoxaline-2-yl-1,4-dioxide pyrid-3-yl-ethenyl ketone

3-Methyl-2-acetylquinoxaline-1,4-dioxide is reacted with pyridine-3-aldehyde as described in Example 1.

3-Methylquinoxaline-2-yl-1,4-dioxide pyrid-3-yl-ethenyl ketone is obtained with a yield of 96%. M.p.: 198°–199° C.

EXAMPLE 5

Quinoxaline-2-yl-1,4-dioxide alpha-naphthylethenyl ketone

2-Acetylquinoxaline-1,4-dioxide is reacted with 1-naphthaldehyde for 5 hours as given in Example 1.

Quinoxaline-2-yl-1,4-dioxide alpha-naphthylethenyl ketone is obtained with a yield of 87%. M.p.: 187°–188° C.

EXAMPLE 6

Quinoxaline-2-yl-1,4-dioxide p-methoxyphenylethenyl ketone

2-Acetylquinoxaline-1,4-dioxide is reacted with p-methoxybenzaldehyde for 16 hours as described in Example 1.

Quinoxaline-2-yl-1,4-dioxide p-methoxyphenylethenyl ketone is obtained with a yield of 76%. M.p.: 169°–170° C.

EXAMPLE 7

3-Methylquinoxaline-2-yl-1,4-dioxide p-methoxyphenylethenyl ketone

3-Methyl-2-acetylquinoxaline-1,4-dioxide is reacted with p-methoxybenzaldehyde as given in Example 1.

3-Methylquinoxaline-2-yl-1,4-dioxide p-methoxyphenylethenyl ketone is obtained with a yield of 86%. M.p.: 186°–187° C.

EXAMPLE 8

3-Methylquinoxaline-2-yl-1,4-dioxide 3-methoxy-4-hydroxy-5-bromophenylethenyl ketone 3-Methyl-2-acetylquinoxaline-1,4-dioxide is reacted with 5-bromovanillin as described in Example 1.

3-Methylquinoxaline-2-yl-1,4-dioxide 3-methoxy-4-hydroxy-5-bromophenylethenyl ketone is obtained with a yield of 81%. M.p.: 212°–213° C.

EXAMPLE 9

Feedstuff concentrate "A" is prepared as follows:

37 kg of wheat bran are blended with 30 kg of 3-methylquinoxaline-2-yl-1,4-dioxide quinoxaline-2-yl-ethenyl 1,4 dioxide ketone prepared as described in Example 3. 3 kg of propylene glycol are sprayed onto the mixture, 2 kg of sorbic acid, 0.5 kg of sodium chloride and 2 kg of fish meal are added and the mixture is stirred for 5 minutes.

120 kg of lucerne meal and 210 kg of VEPEX ® (a green plant feedstuff concentrate) are transferred into another apparatus. 6 kg of propylene glycol are sprayed onto the mixture, 37 kg of concentrate "A" are added with stirring and again 5.5 kg of propylene glycol are sprayed and 85 kg of potato starch are added.

EXAMPLE 10

350 kg of soya meal are stirred with 2.7 kg of soya oil until the soya meal is coated by the oil. 8.2 kg of 3-methylquinoxaline-2-yl-1,4-dioxide quinoxaline-2-yl-ethenyl 1,4-dioxide ketone are added, then homogenized by stirring. Again, 8.2 kg of soya oil are added and the mixture is homogenized by stirring.

EXAMPLE 11

1.2 kg of 3-methylquinoxaline-2-yl-1,4-dioxide quinoxaline-2-yl-ethenyl 1,4-dioxide ketone are added to 90 kg of corn meal under stirring and continuous spraying of 6.2 kg of propylene glycol. Then, 3.2 kg of dicalcium phosphate are added and the mixture is homogenized.

EXAMPLE 12

20 kg of lucerne meal and 30 kg of VEPEX ® are stirred for 1.5 minutes, then 2 kg of maize oil are sprayed onto the mixture in a rate to ensure the uniform addition of oil when the following components are added: 5 kg of 3-methylquinoxaline-2-yl-1,4-dioxide 1,4-dioxide quinoxaline-2-yl-ethenyl ketone, 20 kg of corn starch, 5 kg of 3-methylquinoxaline-2-yl-1,4-dioxide quinoxaline-2-yl-ethenyl 1,4-dioxide ketone, 0.7 kg of silica, 1.3 kg of ascorbic acid, 17 kg of corn starch and again 5 kg of 3-methylquinoxaline-2-yl-1,4-dioxide quinoxaline-2-yl-ethenyl 1,4-dioxide ketone. Then, the mixture is stirred for 5 minutes.

EXAMPLE 13

The process described in Example 9 is repeated with the difference that ethylene glycol is used instead of soya oil.

EXAMPLE 14

Mixture "A"

29 kg of 3-methylquinoxaline-2-yl-1,4-dioxide quinoxaline-2-yl-ethenyl 1,4-dioxide ketone are admixed to 35 kg of potato starch. 0.5 kg of mineral oil are sprayed onto the mixture, then 2 kg of sorbic acid, 3.8 kg of silica and 0.9 kg of calcium propionate are added and the mixture is stirred for another 2 minutes.

42 kg of fish meal and 220 kg of rye bran are blended, 6.3 kg of mineral oil are sprayed onto the mixture and 38 kg of mixture "A," 105 kg of corn flour, 37 kg of mixture "A" and 90 kg of corn flour are added and again 6 kg of mineral oil are sprayed onto the mixture.

EXAMPLE 15

80 kg of wheat bran, 9 kg of 3-methylquinoxaline-2-yl-1,4-dioxide 1,4-dioxide quinoxaline-2-yl-ethenyl ketone, 2.3 kg of calcium carbonate, 0.1 kg of alpha-tocopherole and 0.3 kg of calcium propionate are homogenized with 3 kg propylene glycol.

EXAMPLE 16

100 kg of soya meal, 5.5 kg of 3-methylquinoxaline-2-yl-1,4-dioxide 1,4-dioxide quinoxaline-2-yl-ethenyl ketone and 2.3 kg of butylene glycol are homogenized.

EXAMPLE 17

90 kg of soya flour, 11 kg of 3-methylquinoxaline-2-yl-1,4-dioxide 1,4-dioxide quinoxaline-2-yl-ethenyl ketone, 0.9 kg of silica, 3.2 kg of soya oil and 0.2 kg of calcium propionate are homogenized.

What we claim is:

1. A compound of the formula (I)

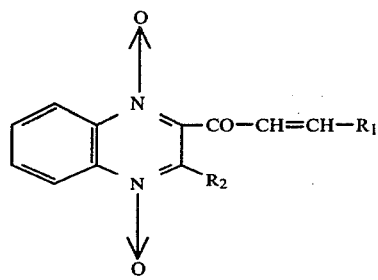

wherein $R_1$ is phenyl, alpha-naphthyl or beta-naphthyl, each of which is unsubstituted or substituted by halogen, hydroxy, $C_1$ to $C_4$ alkyl or $C_1$ to $C_4$ alkoxy, or $R_1$ is 6-benzo[1,3]dioxanyl, quinoxaline-2-yl-1,4-dioxide, or 3-pyridyl, each of which is unsubstituted or substituted by one or two $C_1$ to $C_4$ alkyl groups; and $R_2$ is hydrogen or $C_1$ to $C_4$ alkyl.

2. 3-Methylquinoxaline-2-yl-1,4-dioxide phenylethenyl ketone.

3. 3-Methylquinoxaline-2-yl-1,4-dioxide quinoxaline-2-yl-ethenyl 1,4-dioxide ketone.

4. An antibacterial composition for use in animal husbandry comprising an effective amount of a compound as defined in claim 1, and at least one inert, solid or liquid carrier.

5. An animal feed having antibacterial and/or growth promotion effect containing an effective amount of a compound as defined in claim 1, and at least one inert, solid or liquid carrier.

6. An animal feedstuff concentrate having antibacterial and/or growth promotion effect containing from 0.1 to 25 percent of a compound as defined in claim 1, and at least one inert, solid or liquid carrier.

7. An animal feed additive having antibacterial and/or growth promotion effect containing an effective amount of a compound as defined in claim 1.

8. A process for promoting growth of animals which comprises administering to the animals an effective amount of a compound as defined in claim 1 in an animal feed.

* * * * *